United States Patent

Steiner et al.

[11] Patent Number: 6,028,073
[45] Date of Patent: Feb. 22, 2000

[54] N-SUBSTITUTED 3-AZABICYCLO (3.2.0) HEPTANE DERIVATIVES USEFUL AS NEUROLEPTICS

[75] Inventors: Gerd Steiner, Kirchheim; Rainer Munschauer, Neustadt; Thomas Höger, Edingen-Neckarhausen; Liliane Unger, Ludwigshafen; Hans-Jürgen Teschendorf, Dudenhofen, all of Germany

[73] Assignee: BASF Aktiengesellschaft, Ludwigshafen, Germany

[21] Appl. No.: 08/776,577

[22] PCT Filed: Jul. 21, 1995

[86] PCT No.: PCT/EP95/02893

§ 371 Date: Sep. 18, 1997

§ 102(e) Date: Sep. 18, 1997

[87] PCT Pub. No.: WO96/04272

PCT Pub. Date: Feb. 15, 1996

[30] Foreign Application Priority Data

Aug. 4, 1994 [DE] Germany .............. 44 27 648

[51] Int. Cl.[7] .............. A61K 31/505; C07D 471/02; C07D 401/06
[52] U.S. Cl. .............. 514/258; 514/259; 514/269; 514/270; 514/271; 514/312; 514/414; 514/387; 544/285; 544/282; 544/319; 544/320; 544/321; 546/157; 548/305.1; 548/455

[58] Field of Search .................. 514/258, 259, 514/269, 270, 271, 312, 414, 387; 544/278, 285, 282, 320, 321, 319; 546/157; 548/455, 305.1

[56] References Cited

U.S. PATENT DOCUMENTS 5,475,105  12/1995  Steiner et al. .................. 544/48

*Primary Examiner*—Johann Richter
*Assistant Examiner*—Sonya Wright
*Attorney, Agent, or Firm*—Keil & Weinkauf

[57] ABSTRACT

N-substitued 3-azabicyclo[3.2.0]heptane derivatives of formula (I)

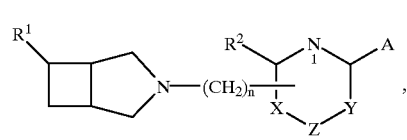

in which $R^1$, $R^2$, A, X, Y and Z have the meanings given in the description, their method of preparation and their use as pharmacological agents.

4 Claims, No Drawings

N-SUBSTITUTED 3-AZABICYCLO (3.2.0) HEPTANE DERIVATIVES USEFUL AS NEUROLEPTICS

This application is a 371 of PCT/EP 95/02893 filed Jul. 21, 1995.

N-Substituted 3-azabicyclo[3.2.0]heptane derivatives, the preparation and use thereof The present invention relates to novel N-substituted azabicycloheptane derivatives, and to their preparation and use for the preparation of pharmaceutical agents.

It is known that N-substituted azabicycloheptane derivatives have surprising affinity for dopamine and serotonin receptor subtypes (DE 42 43 287, DE 42 19 973). The observed high affinities for the $D_4$ dopamine receptor subtype play a special role in this.

We have now found that N-substituted 3-azabicyclo [3.2.0]heptane derivatives of the formula I

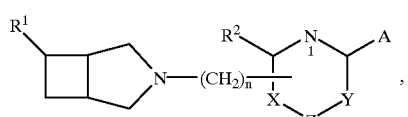

where $R^1$ is naphthyl or phenanthryl which is unsubstituted, mono- or disubstituted by halogen atoms, n is 0, 1, 2, 3 or 4, $R^2$ is hydrogen, hydroxyl, $C_1$–$C_4$-alkyl or C–$C_4$-alkoxy, or together with the adjacent carbon atom is C=O or C=S, X and Y are carbon atoms, CH, $CH_2$, NH or $C_1$–$C_4$-alkyl-N groups or nitrogen atoms, Z is a direct linkage, a CO or CS group or a CH or $CH_2$ group in which one hydrogen atom can be replace d by hydroxyl, amino or $C_1$–$C_4$-alkoxy or a halogen atom, and A is hydrogen, hydroxyl, amino, mercapto, $C_1$–$C_4$-alkylamino, di-$C_1$–$C_4$-alkylamino, $C_1$–$C_4$-alkylthio or $C_1$–$C_4$-alkoxy, or together with the adjacent carbon atom is C=O, or A is a $C_3$–$C_4$-alkylene group which is linked to Y and can contain one or two non-cumulative double bonds and in which one CH or $CH_2$ group can be replaced by a nitrogen or sulfur atom or an NH or N—$CH_3$ group and where the ring can be monosubstituted either by a fluorine or chlorine atom or by methyl, methoxy, nitro or amino, or in the case of a benzene ring the latter can be mono-, di- or trisubstituted by fluorine or chlorine atoms or methyl, trifluoromethyl, nitro, hydroxyl, methoxy, amino, monomethyl- or dimethylamino groups, and where the ring on the right in the formula I can carry a $C_1$–$C_4$-alkyl group on nitrogen atom No. 1 and contain 1 to 3 non-cumulative double bonds, and the salts thereof with physiologically tolerated acids, have valuable pharmacological properties.

The following particular meanings of the substituents $R^1$ and $R^2$ and of n should be mentioned:

$R^1$: naphthyl, unsubstituted or substituted by fluorine or chlorine, $R^2$: methyl and hydroxyl, n: 2.

The ring system on the right in formula I is, in particular,

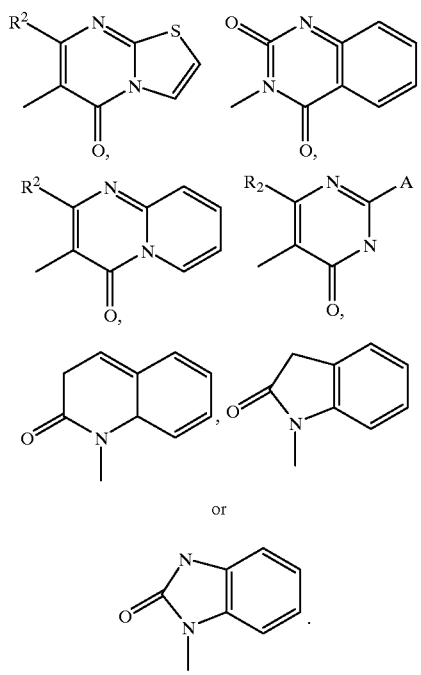

or

Preferred compounds are in particular those in which the ring system on the right of the molecule is derived from 7-methyl-5H-thiazolo[3,2-a]pyrimidin-5-one, 2,4(1H, 3H)-quinazolinedione, 2-methyl-4H-pyrido[1,2-a]pyrimidin-4-one, 2-methylamino-3,6-dimethyl-4(3H)-pyrimidinone, 2(1H)-quinolone, indolin-2-one or 2(3H)-benzimidazolone.

The compounds of the formula I according to the invention can be prepared by reacting a compound of the formula II

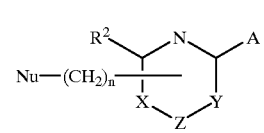

where n, $R^2$, X, Y, Z and A have the abovementioned meanings, and Nu is a nucleofugic leaving group, with a 3-azabicyclo[3.2.0]heptane derivative of the formula III

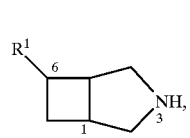

where $R^1$ has the abovementioned meanings, and converting the resulting compound where appropriate into the salt with a physiologically tolerated acid.

Suitable and preferred nucleofugic leaving groups Nu are halogen atoms, in particular bromine or chlorine.

The reaction is expediently carried out in the presence of an inert base such as triethylamine or potassium carbonate to trap acid, in an inert solvent such as a cyclic saturated ether, in particular tetrahydrofuran or dioxane, or an aromatic hydrocarbon such as toluene or xylene.

The reaction normally takes place at from 20 to 150° C., in particular from 80 to 140° C., and is generally complete within 1–10 hours.

The compounds of the formula I according to the invention can be recrystallized [sic] either by recrystallization from conventional organic solvents, preferably from a lower alcohol such as ethanol, or purified by column chromatography.

Racemates can be fractionated to the enantiomers in a simple way by classical resolution using optically active carboxylic acids, eg. tartaric acid derivatives, in an inert solvent, eg. lower alcohols.

The free 3-azabicyclo[3.2.0]heptane derivatives of the formula I can be converted in a conventional way into the salt of a pharmacologically suitable acid, preferably by treating a solution with one equivalent of the appropriate acid. Examples of pharmaceutically suitable acids are hydrochloric acid, phosphoric acid, sulfuric acid, methanesulfonic acid, sulfamic acid, maleic acid, fumaric acid, oxalic acid, tartaric acid or citric acid.

The compounds according to the invention have valuable pharmacological properties. They can be used as neuroleptics (especially atypical), antidepressants, sedatives, hypnotics, CNS protectives or muscle relaxants especially for treating psychoses. A compound according to the invention may display several of said types of action in combination. The pharmacological action is demonstrated both in vivo and in vitro, it being possible to characterize the substances in particular by the affinity, which is in some cases very high and selective, for receptor subtypes, in particular dopamine $D_4$ receptors.

The following methods have been used for the in vivo characterization:

a) Influence on Orientation Motility

In a new environment, mice show an exploratory behavior manifested by increased motor activity. This motor activity is measured in light barrier cages for 0–30 min after the animals (NMRI mice, female) have been placed in the cages. ED50: dose which reduces the motor activity by 50% compared with placebo-treated controls.

b) Apomorphine Antagonism

Female NMRI mice receive 1.21 mg/kg apomorphine s.c. At this dose, apomorphine leads to motor activation manifested by a permanent climbing when the animals are kept in wire mesh cages. The climbing is scored every 2 min for 30 min:

0: animal has four paws on the floor

1: animal has two paws on the wire

2: animal has four paws on the wire (is climbing).

The climbing behavior can be inhibited by pretreatment with antipsychotics.

ED50: dose which inhibits the climbing activity of the animals by 50% compared with placebo-treated controls.

c) Methamphetamine Antagonism

Female NMRI mice receive 1 mg/kg methamphetamine p.o. and, after 30 min, are placed in light barrier cages to measure the motor activity (2 animals/cage, 4 cages/dose). The test substances are given orally 30 min before methamphetamine. The increase in activity due to methamphetamine is calculated for the time from 15 to 60 min after the animals have been placed in the cages as the difference between methamphetamine controls and placebo controls and is set equal to 100%. The ED100 is the dose of test substance which completely abolishes the increase in activity.

d) L-5-HTP Antagonism

Female Sprague-Dawley rats receive L-5-HTP in a dose of 316 mg/kg i.p. The animals then develop an agitation syndrome, of which the symptoms of for paw [sic] treading and tremor are scored (0=absent, 1=moderate, 2=pronounced) every 10 min in the time from 20 to 60 min after administration of L-5-HTP. The average score after administration of L-5-HTP is 17. The test substances are given p.o. 60 min before L-5-HTP. The ED50 is calculated as the dose reducing the control score by 50% on average.

The listed methods are suitable for characterizing substances as antipsychotics; the inhibition of the motor stimulation induced by methamphetamine is particularly regarded as predictive of an antipsychotic effect. A serotonin-antagonistic effect can be revealed by the inhibition of the L-5-HTP syndrome, and this type of effect is characteristic of atypical neuroleptics.

The novel compounds show a good effect in these tests.

The invention accordingly also relates to a therapeutic composition having a content of a compound of the formula I or its pharmacologically suitable acid addition salt as active ingredient in addition to conventional excipients and diluents, and to the use of the novel compounds for controlling diseases.

The compounds according to the invention can be administered orally or parenterally, intravenously or intramuscularly, in a conventional way.

The dosage depends on the age, condition and weight of the patient and on the mode of administration. The daily dose of active ingredient is, as a rule, about 1–100 mg/kg of body weight on oral administration and 0.1–10 mg/kg of body weight on parenteral administration.

The novel compounds can be used in conventional solid or liquid pharmaceutical forms, eg. as uncoated or (film-)coated tablets, capsules, powders, granules, suppositories, solutions, ointments, creams or sprays. These are produced in a conventional way. The active ingredients can for this purpose be processed with conventional pharmaceutical aids such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et. al: Pharmazeutische Technologie, Thieme-Verlag, Stuttgart, 1978). The administration forms obtained in this way normally contain from 1 to 99% by weight of active ingredient.

The substances of the formula II required as starting materials for synthesizing the novel compounds are known or can be synthesized from analogous starting materials by methods described in the literature.

The substances of the formula III can be prepared by subjecting an amine of the formula

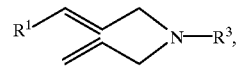

IV where $R^1$ has the abovementioned meanings, and $R^3$ is hydrogen, acetyl, benzyl or trifluoroacetyl, to a photochemical [2+2] cycloaddition and, where appropriate, eliminating an acyl or benzyl group.

The photoreaction takes place well in an inert solvent, preferably acetone, at from 20 to 80° C. A particularly suitable light source is a high-pressure mercury lamp. It may be advantageous to carry out the photocycloaddition in a quartz apparatus under a nitrogen atmosphere with or without the addition of about 1 mole of hydrochloric acid per mole of amine.

The photocycloaddition is in most cases highly diastereoselective to give the bicyclic compounds III with the exo configuration with respect to $R^1$:

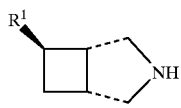

The two enantiomers can be isolated pure by racemate resolution, eg. using optically active tartaric acid derivatives.

An acyl group is eliminated by conventional methods. A similar statement applies to removal of a benzyl group. The amines of the formula IV are disclosed in the literature or can be prepared by either reacting an aldehyde $R^1$—CHO with vinylmagnesium chloride to give the allyl alcohol V

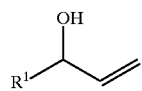

then rearranging with hydrogen chloride to give the allyl chloride VI

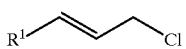

and finally substituting with the appropriate allylamine VII

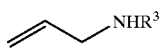

or subjecting a cinnamaldehyde VIII

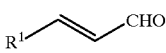

directly to reductive amination with the allylamine VII with $R^3$ equal to hydrogen.

The following examples illustrate the invention:

A Preparation of the Starting Materials aa) 1-(1-Naphthyl)allyl alcohol 277 ml (360 mM [sic]) of a 1.3 M solution of vinylmagnesium chloride in tetrahydrofuran were introduced under nitrogen into a 2 1 stirred flask. Subsequently, while stirring under nitrogen at 30–35° C., a solution of 50 g (320 mM [sic]) of 1-naphthaldehyde dissolved in 250 ml of tetrahydrofuran was added over the course of 60 min. The mixture was then stirred at room temperature under nitrogen for 4.5 h. 90 ml of saturated ammonium chloride solution were then added while stirring and cooling with ice, the mixture was filtered with suction and the residue on the filter was washed three times with 150 ml of tetrahydrofuran. The filtrates were combined, dried with sodium sulfate and concentrated. 58.3 g (99%) of crude product were obtained in the form of a brown oil.

ab) 3-(1-Naphthyl)allyl chloride 58.3 g (317 mM [sic]) of 1-(1-naphthyl)allyl alcohol were dissolved in 400 ml of dichloromethane with stirring. Hydrogen chloride was then passed in to saturation, during which the temperature rose to 37° C. The mixture was then stirred for 1 h. The organic phase was washed with 200 ml of ice-cold water, dried over sodium sulfate and concentrated. 59.2 g (92%) of brownish solid were obtained.

ac) N-Allyl-N-[3-(1-naphthyl)allyl]amine 59.2 g (0.29 M [sic]) of 3-(1-naphthyl)allyl chloride dissolved in 250 ml of toluene were added over the course of 1 h to 167 g (2.9 M [sic]) of allylamine under reflux. The mixture was then refluxed for 2 h. The solution was subsequently concentrated, the residue was taken up in 250-ml of water, and the pH was adjusted to 12 with 50% strength sodium hydroxide solution. The aqueous phase was extracted with dichloromethane, and the organic phase was dried over sodium sulfate and concentrated. Yield: 67.6 g (97%) of dark brown oil.

ad) exo-6-(1-Naphthyl)-3-azabicyclo[3.2.0]heptane 50.0 g (193 mM [sic]) of N-allyl-N-[3-(1-naphthyl)allyl] ammonium chloride were dissolved in 1600 ml of acetone, and 210 ml of 10% strength hydrochloric acid were added. The clear yellow solution was irradiated under nitrogen using a 700 watt high-pressure mercury lamp in a quartz apparatus at room temperature for 4 h. The solution was then concentrated, the residue was taken up with water, and the pH was adjusted to 12 with 50% strength sodium hydroxide solution. The mixture was then stirred for 30 min and extracted twice with tert-butyl methyl ether. The combined organic phases were dried over sodium sulfate and concentrated.

The dark brown oily residue (43.2 g) was dissolved in 150 ml of isopropanol, and 25.5 g (220 mM [sic]) of maleic acid dissolved in 220 ml of isopropanol were added. The precipitated maleate was filtered off with suction, washed with isopropanol and dried in a vacuum oven at 40° C. overnight. Yield: 43.9 g (67%) of colorless powder, melting point 162–164° C. (maleate).

The following substances can be prepared in a similar way:

ae) exo-6-(2-naphthyl)-3-azabicyclo[3.2.0]heptane, melting point 145–147° C. (maleate)

af) exo-6-(5-chloro-1-naphthyl)-3-azabicyclo[3.2.0] heptane, ag) exo-6-(9-phenanthryl)-3-azabicyclo[3.2.0]heptane, ah) exo-6-(6-chloro-2-naphthyl)-3-azobicyclo[3.2.0] heptane.

B Preparation of the Final Products

EXAMPLE 1

3,6-Dimethyl-2-methylamino-5-[2-(exo-6-(2-naphthyl)-3-azabicyclo[3.2.0]heptan-3-yl)ethyl]-3H-pyrimidin-4-one [sic] dihydrochloride 40 2.9 g (13.5 mM [sic]) of 3,6-dimethyl-2-methylamino-5-(2-chloroethyl)-3H-pyrimidin-4-one and 2.8 g (20.3 mM [sic]) of finely powdered potassium carbonate and 0.5 g of potassium iodide were added to 3.0 g (13.5 mM [sic]) of exo-6-(2-naphthyl)-3-azabicyclo-[3.2.0]heptane in 70 ml of xylene and the mixture was refluxed for 12 h.

After cooling and concentration in a rotary evaporator, the residue was partitioned between methylene chloride and water. The aqueous phase was then extracted twice with methylene chloride, and the organic phase was then dried with sodium sulfate and concentrated. The crude product (5.0 g) was purified by column chromatography (silica gel, mobile phase dichloromethane/methanol 90/10).

The free base (2.8 g) was taken up in 150 ml of acetone, and excess ethereal hydrochloric acid was added. The solid hydrochloride was then filtered off with suction under nitrogen in the cold, washed with a little acetone and dried on the funnel under nitrogen. 3.2 g (46%) of product x 2 HCl were isolated, melting point 225–228° C.

The following can be prepared in a similar way:

2. 3,6-dimethyl-2-methylamino-5-[2-(exo-6-(1-naphthyl)-3-azabicyclo[3.2.0]heptan-3-yl)ethyl]-3H-pyrimidin-4-one, melting point 138–140° C. (dihydrochloride),
3. 3,6-dimethyl-2-methylamino-5-[2-(exo-6-(5-chloro-1-naphthyl)-3-azabicyclo[3.2.0]heptan-3-yl)ethyl]-3H-pyrimidin-4-one,
4. 3,6-dimethyl-2-methylamino-5-[2-(exo-6-(6-chloro-2-naphthyl)-3-azabicyclo[3.2.0]heptan-3-yl)ethyl]-3H-pyrimidin-4-one, melting point 260–262° C. (dihydrochloride×2H$_2$O)
5. 3,6-dimethyl-2-methylamino-5-[2-(exo-6-(9-phenanthryl)-3-azabicyclo[3.2.0]heptan-3-yl)ethyl]-3H-pyrimidin-4-one, melting point 255–258° C. (hydrochloride)
6. 7-methyl-6-[2-(exo-6-(2-naphthyl)-3-azabicyclo[3.2.0]heptan-3-yl)ethyl)-5H-thiazolo[3,2-a]pyrimidin-5-one,
7. 3-[2-(exo-6-(2-napthyl)-3-azabicyclo[3.2.0]heptan-3-yl)ethyl]-1H,3H-quinazoline-2,4-dione, melting point 161–164° C.,
8. 3-[2-(exo-6-(1-naphthyl)-3-azabicyclo[3.2.0]heptan-3-yl)-ethyl]-1H,3H-quinazoline-2,4-dione, melting point decomposition above 211° C.,
9. 6-fluoro-3-[2-(exo-6-(1-naphthyl)-3-azabicyclo[3.2.0]heptan-3-yl)ethyl]-1H,3H-quinazoline-2,4-dione, melting point 196–198° C.,
10. 3-[2-(exo-6-(5-chloro-2-naphthyl)-3-azabicyclo[3.2.0]heptan-3-yl)ethyl]-1H,3H-quinazoline-2,4-dione,
11. 3-[2-(exo-6-(1-naphthyl)-3-azabicyclo[3.2.0]heptan-3-yl)ethyl]-2-methyl-4H-pyrido[1.2-a]pyrimidin-4-one,
12. 1-[2-(exo-6-(2-naphthyl)-3-azobicyclo[3.2.0]heptan-3-yl)ethyl]-2(1H)-quinolone,
13. 1-[2-(exo-6-(2-naphthyl)-3-azobicyclo[3.2.0]heptan-3-yl)ethyl]indolin-2-one,
14. 1-[2-(exo-6-(2-naphthyl)-3-azobicyclo[3.2.0]heptan-3-yl)ethyl]-2(3H)-benzimidazolone,
15. 1-[2-(exo-6-(2-naphthyl)-3-azobicyclo[3.2.0]heptan-3-yl)ethyl]-3-methyl-2(3H)-benzimidazolone.

We claim:

1. An N-substituted 3-azabicyclo[3.2.0]heptane derivative of the formula I

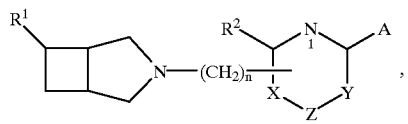

where

R$^1$ is naphthyl or phenanthryl which is unsubstituted, mono- or disubstituted by halogen atoms, n is 0, 1, 2, 3 or 4, R$^2$ is hydrogen, hydroxyl, C$_1$–C$_4$-alkyl or C$_1$–C$_4$-alkoxy, or together with the adjacent carbon atom is C=O or C=S, X and Y are carbon atoms, CH, CH$_2$, NH or C$_1$–C$_4$-alkyl-N groups or nitrogen atoms, Z is a direct linkage, a CO or CS group or a CH or CH$_2$ group in which one hydrogen atom can be replaced by hydroxyl, amino or C$_1$–C$_4$-alkoxy or a halogen atom, and A is hydrogen, hydroxyl, amino, mercapto, C$_1$–C$_4$-alkylamino, di-C$_1$–C$_4$-alkylamino, C$_1$–C$_4$-alkylthio or C$_1$–C$_4$-alkoxy, or together with the adjacent carbon atom is C=O, or A is a C$_3$–C$_4$-alkylene group which is linked to Y and can contain one or two non-cumulative double bonds and in which one CH or CH$_2$ group can be replaced by a nitrogen or sulfur atom or an NH or N—CH$_3$ group and where the ring can be monosubstituted either by a fluorine or chlorine atom or by methyl, methoxy, nitro or amino, or in the case of a benzene ring the latter can be mono-, di- or trisubstituted by fluorine or chlorine atoms or methyl, trifluoromethyl, nitro, hydroxyl, methoxy, amino, monomethyl- or dimethylamino groups, and where the ring on the right in the formula I can carry a C$_1$–C$_4$-alkyl group on nitrogen atom No. 1 and contain 1 to 3 non-cumulative double bonds, and the salts thereof with physiologically tolerated acids.

2. A pharmaceutical composition comprising an effective amount of the compound I defined in claim 1 and pharmaceutically acceptable auxiliaries.

3. A method of treating psychoses, which method comprises administering to a patient in need of such treatment an effective amount of the compound I defined in claim 1.

4. A method of preparing the compound I defined in claim 1, which method comprises reacting a compound of the formula II

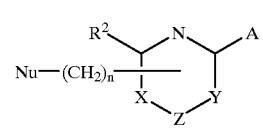

where n, R$^2$, X, Y, Z, and A are defined in claim 1 and Nu is a nucleofugic leaving group; with a 3-azabicyclo[3.2.0] heptane derivative of the formula III

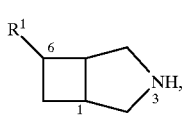

where R$^1$ is defined in claim 1; and converting the resulting compound into its salt with a pharmacologically tolerated acid.

* * * * *